United States Patent
Samain et al.

(10) Patent No.: US 10,588,831 B2
(45) Date of Patent: Mar. 17, 2020

(54) LIGHTENING PROCESS USING A SUBSTRATE BEARING AT LEAST ONE OXIDIZING AGENT AND AN AQUEOUS COMPOSITION

(71) Applicant: L'OREAL, Paris (FR)

(72) Inventors: Henri Samain, Bievres (FR); Philippe Rapold, Paris (FR)

(73) Assignee: L'OREAL, Paris (FR)

( * ) Notice: Subject to any disclaimer, the term of this patent is extended or adjusted under 35 U.S.C. 154(b) by 26 days.

(21) Appl. No.: 15/108,462

(22) PCT Filed: Dec. 29, 2014

(86) PCT No.: PCT/EP2014/079396
§ 371 (c)(1),
(2) Date: Jun. 27, 2016

(87) PCT Pub. No.: WO2015/097309
PCT Pub. Date: Jul. 2, 2015

(65) Prior Publication Data
US 2016/0324731 A1    Nov. 10, 2016

(30) Foreign Application Priority Data
Dec. 27, 2013  (FR) ..................................... 13 63656

(51) Int. Cl.
| | | |
|---|---|---|
| A61K 8/02 | (2006.01) | |
| A61Q 5/08 | (2006.01) | |
| A45D 19/00 | (2006.01) | |
| A61K 8/22 | (2006.01) | |
| A61K 8/23 | (2006.01) | |
| A61K 8/25 | (2006.01) | |
| B44C 1/165 | (2006.01) | |
| B41M 5/025 | (2006.01) | |

(52) U.S. Cl.
CPC ........ *A61K 8/0204* (2013.01); *A45D 19/0025* (2013.01); *A61K 8/22* (2013.01); *A61K 8/23* (2013.01); *A61K 8/25* (2013.01); *A61Q 5/08* (2013.01); *B44C 1/165* (2013.01); *A45D 2019/0075* (2013.01); *A45D 2019/0091* (2013.01); *A61K 2800/56* (2013.01); *A61K 2800/5922* (2013.01); *A61K 2800/87* (2013.01); *A61K 2800/884* (2013.01); *B41M 5/025* (2013.01)

(58) Field of Classification Search
None
See application file for complete search history.

(56) References Cited

U.S. PATENT DOCUMENTS

| | | |
|---|---|---|
| 4,003,699 A | 1/1977 | Rose et al. |
| RE30,199 E | 1/1980 | Rose et al. |
| 5,061,289 A | 10/1991 | Clausen et al. |
| 5,380,340 A | 1/1995 | Neunhoeffer et al. |
| 5,534,267 A | 7/1996 | Neunhoeffer et al. |
| 5,663,366 A | 9/1997 | Neunhoeffer et al. |
| 5,766,576 A | 6/1998 | Löwe et al. |
| 5,931,168 A | 8/1999 | Abercrombie et al. |
| 6,099,592 A | 8/2000 | Vidal et al. |
| 6,284,003 B1 | 9/2001 | Rose et al. |
| 6,338,741 B1 | 1/2002 | Vidal et al. |
| 6,645,258 B2 | 11/2003 | Vidal et al. |
| 6,730,789 B1 | 5/2004 | Birault et al. |
| 2002/0050013 A1 | 5/2002 | Vidal et al. |
| 2003/0019051 A9 | 1/2003 | Vidal et al. |
| 2005/0028302 A1 | 2/2005 | Audousset et al. |
| 2008/0083420 A1* | 4/2008 | Glenn ................ A45D 19/0008 132/208 |
| 2009/0050171 A1 | 2/2009 | Barrass et al. |
| 2013/0074863 A1 | 3/2013 | Kleen et al. |
| 2014/0352714 A1 | 12/2014 | Samain |

FOREIGN PATENT DOCUMENTS

| | | |
|---|---|---|
| EP | 0770375 A1 | 5/1997 |
| FR | 2886136 A1 | 12/2006 |
| GB | 1026978 A | 4/1966 |
| GB | 1153196 A | 5/1969 |
| JP | 02-019576 A | 1/1990 |
| JP | 05-163124 A | 6/1993 |
| JP | 2006-224517 A | 8/2006 |
| WO | 94/08969 A1 | 4/1994 |
| WO | 94/08970 A1 | 4/1994 |

(Continued)

OTHER PUBLICATIONS

Non-Final Office Action for copending U.S. Appl. No. 15/108,492, dated May 2, 2017.

(Continued)

*Primary Examiner* — Nicole P Babson

(74) *Attorney, Agent, or Firm* — The Marbury Law Group, PLLC

(57) ABSTRACT

The present invention relates to the field of lightening keratin fibres and more particularly to the field of lightening the hair. The present invention relates to a process for lightening keratin fibres, in particular human keratin fibres such as the hair, which consists in using on the said fibres i) a substrate comprising on its surface one or more chemical oxidizing agents preferably in solid form, and ii) an aqueous composition preferably comprising one or more chemical oxidizing agents. The present invention also relates to a process for preparing the said substrate thus pretreated.

14 Claims, No Drawings

(56) References Cited

FOREIGN PATENT DOCUMENTS

| WO | 96/15765 A1 | 5/1996 |
| WO | 03/041531 A1 | 5/2003 |
| WO | 2013/093775 A1 | 6/2013 |
| WO | 2015/097307 A1 | 7/2015 |

OTHER PUBLICATIONS

Final Office Action for copending U.S. Appl. No. 15/108,492, dated Nov. 24, 2017.
Notice of Allowance for copending U.S. Appl. No. 15/108,492, dated Jun. 8, 2018.
International Search Report for PCT/EP2014/079394, dated Mar. 17, 2015.
International Search Report for PCT/EP2014/079396, dated Mar. 17, 2015.
PCT/IB/304 Form for PCT/EP2014/079394, dated Feb. 27, 2015.
PCT/IB/304 Form for PCT/EP2014/079396, dated Jan. 19, 2015.

* cited by examiner

LIGHTENING PROCESS USING A SUBSTRATE BEARING AT LEAST ONE OXIDIZING AGENT AND AN AQUEOUS COMPOSITION

CROSS REFERENCE TO RELATED APPLICATIONS

This is a national stage application of PCT/EP2014/079396, filed internationally on Dec. 29, 2014, which claims priority to French Application No. 1363656, filed on Dec. 27, 2013, both of which are incorporated by reference herein in their entireties.

The present invention relates to the field of lightening keratin fibres and more particularly to the field of lightening the hair.

The present invention relates to a process for lightening keratin fibres, in particular human keratin fibres such as the hair, which consists in using on the said fibres i) a substrate comprising on its surface one or more chemical oxidizing agents, and ii) an aqueous composition preferably comprising one or more chemical oxidizing agents.

The present invention also relates to a process for preparing the substrate as described previously, used via a printing method.

The invention also relates to an element in sheet form pretreated with a composition comprising one or more oxidizing agents in solid form.

The lightening of keratin fibres, in particular of human keratin fibres such as the hair, is performed by oxidation of the "melanin" pigment resulting in the dissolution and the partial or total removal of this pigment.

Standard processes for lightening human keratin fibres generally consist in applying an aqueous composition comprising at least one oxidizing agent, under alkaline pH conditions in the vast majority of cases. The role of this oxidizing agent is especially to degrade the melanin of the keratin fibres, which, depending on the nature of the oxidizing agent present, leads to more or less pronounced lightening of the fibres.

Thus, to obtain relatively weak lightening, the oxidizing agent is generally hydrogen peroxide. When more pronounced lightening is sought, it is known practice to use bleaching powders based on peroxygenated salts such as ammonium or alkali metal persulfates, perborates or percarbonates, which are combined at the time of use with an aqueous hydrogen peroxide composition.

However, it has been found that it is often difficult or even impossible to obtain lightening on keratin fibres which has novel visual results by using the standard processes described previously. In particular, these processes often have the defect of not satisfactorily producing bleached patterns, which may give rise to novel optical effects on the entire head of hair, and which are both sharp and precise.

These processes also entail the risk of not leading to the final lightening desired by the user because of an error that may arise during the handling of the oxidizing compositions.

It has also been found that the storage of oxidizing compositions may pose problems of space occupation and/or of storage over the long term, especially in hairstyling salons.

Furthermore, bleaching powders have a tendency to form dust during their handling, transportation and storage. Now, the products of which they are composed, such as persulfates, are aggressive and in particular irritant to the eyes, the respiratory pathways and mucous membranes.

Moreover, it is already known practice from document FR 2 984 087 to use a dyeing or bleaching process which consists in placing keratin fibres in contact with a substrate bearing a bleaching or dye composition having a formulation that changes depending on the position on the said substrate, so as to obtain shaded dyeing or bleaching.

However, the said document does not describe a process that is capable of producing precise patterns and/or of leading to unified bleaching results.

There is thus a real need to perform a process for lightening keratin fibres, in particular human keratin fibres such as the hair, which does not have the drawbacks mentioned previously, i.e. which is especially capable of giving on the said fibres lightening that may be unified and/or that may have novel visual results, in particular precise patterns, of reducing the problems of space occupation and/or storage of the compositions used, of minimizing the risks of contact that may arise between the compositions used and the user, and also the risks of not obtaining the desired lightening.

This aim is achieved by the present invention, one subject of which is especially a process for lightening keratin fibres, in particular human keratin fibres such as the hair, which consists in applying successively on the said fibres i) a substrate comprising on its surface one or more chemical oxidizing agents, preferably in solid form, and ii) an aqueous composition preferably comprising one or more chemical oxidizing agents.

Hence according to the present invention, the substrate and the aqueous composition are successively applied on the keratin fibres.

In others words, the substrate may be applied first on the keratin fibres and then the aqueous composition is applied on the said fibres or the aqueous composition is first applied on the keratin fibres and then the substrate is applied.

The process for lightening keratin fibres thus uses a substrate onto which has been deposited one or more chemical oxidizing agents, preferably in solid form. In other words, the substrate has been pretreated on its surface with an oxidizing composition containing one or more chemical oxidizing agents.

Thus, in the course of placing the keratin fibres in contact with the pretreated substrate and the aqueous composition, the oxidizing agents present on the surface of the substrate dissolve, in contact with the said fibres, to lighten them, which can lead to lightening that may be unified and/or to bleached patterns.

In particular, the oxidizing agent(s) are deposited on the surface of the substrate and may be localized in certain places on the said surface so as to represent one or more geometrical forms in order thereafter to produce one or more bleached patterns on the keratin fibres after contact between the said fibres, the pretreated substrate and the aqueous composition. In other words, the substrate may be pretreated in places with an oxidizing composition containing one or more oxidizing agents so as to be able to produce one or more patterns on the fibres.

The lightening process according to the invention thus makes it possible to produce on the keratin fibres, with great precision, bleached patterns that are visually sharp. In particular, this process makes it possible to produce millimetre-sized bleached patterns having all types of shapes, such as dots or waves, which are easily reproducible. These patterns may also lead to novel optical effects when they are then repeated over the entire head of hair.

In other words, the process according to the invention makes it possible to obtain patterns, especially millimetre-sized patterns, homogeneously over the entire head of hair, or in a localized manner on a part of the head of hair. These patterns may be imaginative from an aesthetic viewpoint or may serve to hide an irregularity in the colour or appearance of the keratin fibres, especially in the case of hair regrowth or fading of the ends.

This process also has the advantage of being able to retreat heads of hair that have already been dyed or bleached to compensate for the hair regrowth, to rectify errors arising during a prior bleaching, to rectify the effect of natural bleaching or to attenuate in a localized or unified manner a prior dyeing.

Moreover, by means of using substrates comprising one or more oxidizing agents, i.e. substrates that are pretreated with a composition containing such oxidizing agents, this process makes it possible to reduce the risks of interactions with the user's hands, scalp, face and/or clothing. This process also makes it possible to avoid the problems of running and/or errors in application of the compositions.

Similarly, by means of applying such pretreated substrates, this process makes it possible to reduce the problem of storage of the compositions used in standard lightening processes, which makes it possible to substantially reduce the problems of space occupation. In particular, the user may have at his disposal a larger number of substrates pretreated with oxidizing agents while at the same time saving space in the hairstyling salons.

Moreover, the process according to the invention has the advantage of using pretreated substrates that can be satisfactorily stored over a period of time that may range, for example, from a few days to several months.

The lightening process according to the invention also has the advantage of minimizing the risks of errors that may arise during the handling of the oxidizing compositions.

The lightening process according to the invention also has improved lightening performance qualities.

When the aqueous composition contains one or more chemical oxidizing agents, the process according to the invention has the advantage of leading to precise bleached patterns that are even more markedly distinguished on the head of hair.

The present invention also relates to a process for preparing a substrate containing at its surface one or more oxidizing agents, preferably in solid form, which consists in depositing, via a printing method, an oxidizing composition containing one or more oxidizing agents onto a substrate.

In other words, the oxidizing composition is printed onto the surface of a substrate by means of the use of a printing process so as to obtain a pretreated substrate.

The substrate obtained is thus surface-treated with the said composition based on oxidizing agents before being used in the lightening process according to the invention.

The printing method which serves to deposit the oxidizing composition onto the surface of a substrate may be a screen printing process, a flexography process, an offset printing process or a printing process using an inkjet printer or a laser printer.

This preparation process may be performed in the hairstyling salon itself, especially by means of the presence of an inkjet printer, before performing the lightening process according to the invention.

The production of these pretreated substrates in the hairstyling salon itself and/or in the user's home has the advantage of minimizing the problems of preservation, especially with regard to oxygen, since the user and/or the hairstylist will be able to use the substrates within minutes or hours of producing them.

Alternatively, this process may also be performed outside the hairstyling salon and as such the user merely has to use the substrates to lighten the hair.

In this case, the pretreated substrate may be supplied to the user to produce a unified lightening effect and/or bleached patterns on the hair.

The invention also relates to an element in sheet form pretreated on its surface with a composition comprising one or more oxidizing agents.

The said composition is printed on the surface of the element in sheet form.

In other words, another subject of the present invention relates to an element in sheet form comprising on its surface one or more oxidizing agents.

In particular, the element in sheet form comprises one or more oxidizing agents that have been printed onto its surface.

The element in sheet form according to the invention has the advantage of being easy to apply to locks of hair. In particular, such an element may be positioned with great precision at the place where it is desired to produce the bleached pattern(s) on the locks of hair.

The element in sheet form has the advantage of being able to be easily stored in the user's home when compared with the use of oxidizing compositions used in standard lightening processes, thereby making it possible to substantially reduce the space occupation.

Moreover, the element in sheet form may be prepared directly in the hairstyling salon or beforehand.

Other subjects, characteristics, aspects and advantages of the invention will emerge even more clearly on reading the description and the examples that follow.

As indicated previously, the lightening process uses on the said fibres a substrate that has been pretreated on its surface with a composition containing one or more chemical oxidizing agents.

The substrate used in the process of the present invention is preferably dry.

According to the present invention, the term "dry" means that the substrate does not comprise volatiles solvents to less than 5 mg per cm$^2$, preferably less than 1 mg per cm$^2$ of the said substrate.

According to the present invention, the terms "volatiles solvents" mean that the solvents have a boiling temperature of less than 140° C.

The substrate may be in the form of an element in sheet form or in another embodiment.

According to a preferred embodiment, the substrate is an element in sheet form.

The element in sheet form may be produced of plastic material, in particular thermoplastic, paper, a metal, especially aluminium, a woven, a nonwoven of non-absorbent fibres, especially of cellulose or a derivative thereof, or polyamide 6,6.

Preferably, the element in sheet form is a sheet of plastic material, especially of thermoplastic, or a nonwoven material of non-absorbent fibres, especially a nonwoven based on cellulose or a derivative thereof.

In particular, the element in sheet form used in the lightening process is a plastic sheet.

The element in sheet form may consist of a water-soluble material, which makes it possible, for example, to remove it by washing the hair.

Preferably, the element in sheet form comprises an assembly of a layer of a water-soluble material and a layer of a non-water-soluble material, for example an aluminium foil.

The support may be designed to be able to be closed around a lock of hair. In this case, such a substrate is, for example, provided with a fastening means for keeping it in such a state, for example an adhesive disposed close to one edge or a mechanical attachment relief.

Preferably, the element in sheet form has a basis weight ranging from 20 to 300 g/m2 and even more preferentially ranging from 30 to 200 g/m2.

The element in sheet form especially has a thickness ranging from 40 to 1000 micrometres, preferably a thickness ranging from 40 to 400 micrometres and better still from 60 to 200 micrometres.

The element in sheet form may be opaque or transparent. Preferably, the element in sheet form is transparent, which facilitates its positioning on the hair, especially when it is desired to produce one or more patterns at a precise place on the lock or on the head of hair. In other words, the transparency of the element in sheet form facilitates the implementation of the lightening process, especially in the production of bleached patterns, and improves its precision.

The element in sheet form used in the lightening process according to the invention is preferably flexible and strong. Preferentially, the strength of the sheet is greater than 300 kPa (standard TAPPI-T403).

Preferably, the element in sheet form is water-resistant. In particular, the water absorption of the said element is measured by the COBB 60 test which corresponds to the capacity of the said element to absorb water during contact for 60 seconds (the procedure of which is given by standard ISO 535, TAPPI-T411 measurement).

Thus, the element in sheet form absorbs less than 100 g/m2 and preferentially less than 40 g/m2 of water.

Preferably, the element in sheet form is resistant to the oily compounds. Thus, use may be made of a "food" paper, i.e. a complex of paper and of polymeric compound of the polyethylene type or of paper and paraffin, which is capable of acting as a barrier to water and to oils.

The element in sheet form may optionally be covered with a deposit of an adhesive composition. This adhesive layer makes it possible to improve the adhesion of the oxidizing agent(s) to the surface of the element in sheet form.

According to a preferred embodiment, the element in sheet form, after treatment with the composition containing one or more oxidizing agents, may be covered with a protection means which serves to protect the surface of the said element from external elements. Thus, the element in sheet form comprises one or more oxidizing agents that may be covered with a protective layer. Such a protective layer makes it possible to minimize the impairment of the oxidizing agent(s) caused by moisture, light or atmospheric oxygen.

Thus, the element in sheet form may be protected by implementing processes used in paper varnishing techniques (oil varnish, acrylic varnish, etc.), and in particular by using a water-based or organic acrylic varnish.

In this way, the element in sheet form containing one or more oxidizing agents may be surface-protected with a layer of acrylic varnish.

In accordance with this embodiment, the element in sheet form contains one or more oxidizing agents preferably in solid form and is covered with a layer of acrylic varnish. In other words, the element in sheet form contains a layer containing one or more oxidizing agents and a layer of acrylic varnish, the two layers being juxtaposed one on the other.

The mass per unit area of the layer of acrylic varnish ranges from 1 to 10 g/m2 and more particularly from 2 to 5 g/m2.

According to one variant, the element in sheet form is covered with a detachable protective sheet. To do this, the edges of the element in sheet form and of the protective sheet are bonded together by means of a fastening means, especially an adhesive, which may be produced via any type of method, especially by heat sealing. Thus, good cohesion is ensured between the protective sheet and the element in sheet form.

Advantageously, the protective sheet is UV-opaque to ensure better protection.

According to another variant, the element in sheet form may be covered by another protective means, namely a hermetic wrapping, defining above the element a space without oxygen (under vacuum or under an inert atmosphere).

As indicated previously, the substrate comprises on its surface one or more chemical oxidizing agents.

The oxidizing agent(s) may be present on all or part of the surface of the substrate. Thus, the surface of the substrate may be entirely or partially covered with a layer containing one or more oxidizing agents. This layer represents a treatment layer of the surface of the substrate.

The expression "chemical oxidizing agent" means an oxidizing agent other than atmospheric oxygen.

The chemical oxidizing agent(s) may be chosen from hydrogen peroxide, urea peroxide, alkali metal bromates or ferricyanides, peroxygenated salts, for instance alkali metal or alkaline-earth metal persulfates, perborates and percarbonates, and also peracids and precursors thereof.

Preferably, the chemical oxidizing agent(s) are chosen from solid chemical oxidizing agents, and more preferentially from urea peroxide, alkali metal bromates or ferricyanides, or peroxygenated salts, for instance alkali metal or alkaline-earth metal persulfates, perborates and percarbonates.

Better still, the oxidizing agent(s) are chosen from peroxygenated salts and even more preferentially from persulfates.

The chemical oxidizing agent(s) may be advantageously present in a content ranging from 0.01% to 100% by weight, preferably in a content ranging from 10% to 90% by weight and better still ranging from 20% to 80% relative to the weight of the treatment layer of the surface of the substrate.

The chemical oxidizing agent(s) may be present on all or, preferably, on part of the surface of the substrate. Thus, the surface of the substrate may be entirely or partially covered with a layer containing one or more chemical oxidizing agents.

Preferably, the chemical oxidizing agent(s) are deposited on a part of the surface of the substrate and represent patterns which, after contact with the keratin fibres and the aqueous composition, will make it possible to produce the bleached patterns on the said fibres. In other words, the oxidizing agent(s) are deposited in the form of patterns on the surface of the substrate. Thus, the surface of the substrate comprises one or more oxidizing agents arranged in one or more particular geometrical forms, known as patterns, which, after contact with the aqueous composition, lead to the production of bleached patterns on the said fibres.

The pattern(s) may have any form, especially a geometrical form.

Thus, the oxidizing agent(s) are present on a part of the surface of the substrate and represent patterns having the desired form.

The substrate may comprise on the face opposite the face bearing the oxidizing agent(s) a copy of the pattern(s) having the desired form. The production of these patterns on the opposite face makes it possible to indicate the place where the oxidizing agent(s) may then be deposited on the surface of the substrate. Such a production facilitates thereafter the emplacement of the substrate on the keratin fibres at the place where it is desired to produce the pattern.

As a variant, such patterns are produced on the surface of the substrate before the pretreatment so as to deposit thereafter the oxidizing agent(s) directly on the patterns. In other words, the patterns that it is desired to obtain on the keratin fibres may be produced beforehand on the surface of the substrate intended to be pretreated.

In both cases, the production of patterns on the surface of the substrate intended to be pretreated or on the surface opposite the pretreated surface is all the more advantageous when the substrate used is transparent.

In particular, the patterns may be printed beforehand on the substrate.

The substrate may also comprise on its surface one or more alkaline agents. In other words, the substrate may be pretreated with an oxidizing composition comprising one or more chemical oxidizing agents and one or more alkaline agents.

The alkaline agents may be chosen from carbonates, alkanolamines such as monoethanolamine, diethanolamine, triethanolamine and derivatives thereof, oxyethylenated and/or oxypropylenated ethylenediamines, mineral or organic hydroxides, alkali metal silicates such as sodium metasilicates, amino acids, preferably basic amino acids such as arginine, lysine, ornithine, citrulline and histidine, and the compounds of formula (I) below:

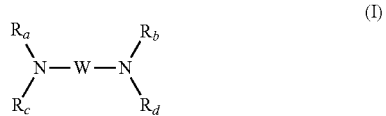

in which:

W is a divalent (C1-C8)alkylene group, preferably a propylene group, optionally substituted especially with a hydroxyl group or a C1-C4 alkyl radical;

Ra, Rb, Rc and Rd, which may be identical or different, represent a hydrogen atom or a C1-C4 alkyl or C1-C4 hydroxyalkyl radical.

The mineral or organic hydroxides are preferably chosen from i) hydroxides of an alkali metal, ii) hydroxides of an alkaline-earth metal, for instance sodium hydroxide or potassium hydroxide, iii) hydroxides of a transition metal, such as hydroxides of metals from groups III, IV, V and VI, iv) hydroxides of lanthanides or actinides, quaternary ammonium hydroxides and guanidinium hydroxide.

The hydroxide may be formed in situ, for instance guanidine hydroxide, formed by reacting calcium hydroxide with guanidine carbonate.

In particular, the alkaline agents used are solid in the dry state.

In a first variant of the invention, the alkaline agents are solid before use in the oxidizing composition, and are preferably chosen from carbonates, mineral hydroxides such as soluble sodium or potassium hydroxides or silicates.

In another variant of the invention, the alkaline agents are chosen from alkanolamines, in particular monoethanolamine, diethanolamine and triethanolamine.

The alkaline agent(s) may be present in a content ranging from 0.01% to 20% by weight relative to the total weight of the treatment layer of the surface of the substrate.

The alkaline agent(s) may be present in a content ranging from 0.01% to 20% by weight relative to the total weight of the treatment oxidizing composition of the surface of the substrate.

The oxidizing composition may be aqueous or anhydrous.

When the oxidizing composition is aqueous and contains one or more alkaline agents, the pH preferably ranges from 7.5 to 13, better still from 8 to 12 and even better still from 8 to 11.

The substrate may also comprise one or more compounds such as acids, and in particular citric acid.

The active agent(s) may be present in a content ranging from 1% to 20% by weight relative to the weight of the chemical oxidizing agents, both relative to the treatment composition and relative to the surface layer after pretreatment.

The oxidizing composition may contain one or more organic solvents.

Organic solvents that may be mentioned include linear or branched and preferably saturated monoalcohols or diols, comprising 2 to 6 carbon atoms, such as ethyl alcohol, isopropyl alcohol, hexylene glycol (2-methyl-2,4-pentanediol), neopentyl glycol and 3-methyl-1,5-pentanediol, butylene glycol, dipropylene glycol and propylene glycol; aromatic alcohols such as benzyl alcohol or phenylethyl alcohol; polyols containing more than two hydroxyl functions, such as glycerol; polyol ethers, for instance ethylene glycol or propylene glycol monomethyl, monoethyl or monobutyl ether; and also diethylene glycol alkyl ethers, especially C1-C4 alkyl ethers, for instance diethylene glycol monoethyl ether or monobutyl ether.

The element may also comprise on the surface of the substrate a deposit of one or more activators or catalysts. In particular, the substrate comprises a deposit of one or more metal salts in a content ranging from 1% to 20% by weight relative to the weights of the chemical oxidizing agents.

The substrate used in the lightening process is pretreated with an oxidizing composition containing one or more oxidizing agents.

Preferably, the substrate is pretreated with an oxidizing composition containing one or more oxidizing agents and one or more alkaline agents.

The oxidizing composition may be liquid or in powder form, preferably in powder form.

The oxidizing composition deposited on the surface of the substrate may optionally result from successive treatments of the substrate with one or more oxidizing agents, on the one hand, one or more alkaline agents, on the other hand, and optionally one or more active agents as described previously.

As indicated previously, the lightening process uses an aqueous composition which interacts with the substrate comprising on its surface one or more oxidizing agents.

Preferably, this aqueous composition contains one or more chemical oxidizing agents.

In particular, the oxidizing agent(s) are chosen from hydrogen peroxide, urea peroxide, alkali metal bromates or ferricyanides, peroxygenated salts, for instance alkali metal or alkaline-earth metal persulfates, perborates and percarbonates, and also peracids and precursors thereof.

Even more preferentially, the oxidizing agent is hydrogen peroxide.

This oxidizing agent advantageously consists of hydrogen peroxide especially as an aqueous solution (aqueous hydrogen peroxide solution), the concentration of which may range more particularly from 0.1% to 50% by weight, even more preferentially from 0.5% to 20% by weight and better still from 1% to 15% by weight relative to the total weight of the aqueous composition.

Preferably, this aqueous composition also contains one or more alkaline agents, especially the alkaline agents as described previously.

The use of an oxidizing aqueous composition containing one or more alkaline agents in the course of the lightening process according to the invention can especially lead to an improved lightening effect on the treated keratin fibres, which reinforces the visibility of the pattern(s) obtained.

The composition may also comprise one or more thickeners, especially nonionic thickeners.

According to one embodiment, the lightening process thus consists in placing the keratin fibres in contact with the substrate comprising on its surface one or more chemical oxidizing agents, and in then applying to the said fibres the aqueous composition preferably containing one or more oxidizing agents.

In particular, the keratin fibres are placed on the surface of the substrate bearing the oxidizing agent(s), i.e. at the place where the surface of the substrate is covered with the oxidizing agent(s), and the aqueous composition is then applied to the said fibres. The oxidizing agents are thus dissolved and lighten the keratin fibres.

The aqueous composition may be applied using an applicator, in particular a brush, or by hand.

In accordance with this embodiment, after applying the aqueous composition, the locks of hair thus treated may be protected with a paper to protect the other locks that have not been treated.

According to another embodiment, the lightening process consists in applying an aqueous composition preferably containing one or more oxidizing agents to the keratin fibres and then in applying to the said fibres a substrate comprising on its surface one or more oxidizing agents.

In this embodiment, the order of application between the pretreated substrate and the aqueous composition is thus inverted relative to the preceding embodiment.

In this embodiment, the keratin fibres are especially placed on a support, for example the upper surface of a sheet of paper, the aqueous composition is applied to the said fibres and the substrate pretreated with one or more oxidizing agents is then applied to the said fibres. The oxidizing agents present on the surface of the substrate are thus dissolved and lighten the covered keratin fibres.

In accordance with this embodiment, the substrate pretreated with one or more oxidizing agents is applied to the keratin fibres treated with the aqueous composition so that the surface containing the oxidizing agent(s) is in contact with the fibres.

The substrate pretreated with one or more oxidizing agents may be applied to the keratin fibres for a time ranging from 5 to 60 minutes and preferably ranging from 10 to 30 minutes.

The aqueous composition may be applied to the keratin fibres for a time ranging from 5 to 60 minutes and preferably ranging from 10 to 30 minutes.

The substrate and the aqueous composition may be applied at room temperature (25° C.), optionally with raising of the temperature, which may be up to 60° C.

After the treatment, the human keratin fibres are optionally rinsed with water, optionally washed with a shampoo and then rinsed with water, before being dried or left to dry.

According to an advantageous embodiment, the lightening process consists in using i) a substrate comprising on its surface one or more chemical oxidizing agents in solid form, chosen from peroxygenated salts, preferably persulfates, and ii) an aqueous composition comprising one or more chemical oxidizing agents chosen from hydrogen peroxide.

In accordance with this embodiment, the substrate and the aqueous composition are successively applied on the keratin fibres.

In accordance with this embodiment, the substrate advantageously comprises on its surface one or more alkaline agents.

In accordance with this embodiment, the substrate is advantageously an element in sheet form.

The present invention also relates to a process for preparing the substrate as described previously, which consists in depositing, via a printing method, an oxidizing composition containing one or more chemical oxidizing agents onto the surface of a substrate.

In other words, the oxidizing composition is printed onto the surface of a substrate so as to obtain a substrate containing on its surface one or more chemical oxidizing agents.

Preferably, the oxidizing composition used in the process for preparing the substrate comprises one or more oxidizing agents in a content ranging from 0.01% to 100% by weight, preferably from 10% to 90% by weight and better still from 20% to 80% by weight relative to the total weight of the said composition.

More preferentially, the oxidizing composition comprises one or more oxidizing agents and one or more alkaline agents.

According to one embodiment, the process for preparing the substrate consists in depositing the composition containing the chemical oxidizing agent(s) onto the surface of a substrate covered with a deposit of an adhesive layer. This adhesive layer may cover all or part of the substrate. In particular, the adhesive layer may represent a pattern.

According to one embodiment, the process for preparing the substrate as described previously consists in partially depositing onto the surface of a substrate, via a printing method, an oxidizing composition containing one or more chemical oxidizing agents.

In accordance with this embodiment, the oxidizing agent(s) are deposited in the form of one or more patterns onto the surface of a substrate.

In particular, the patterns may be squares, circles, ovals, ellipses or triangles, in the form of filled patterns or of lines surrounding these patterns.

They may also be thick or thin, straight or curved lines, crossed lines, representing letters, stylized drawings or geometrical patterns.

They may also be dotted lines or spots.

The printing method serving to deposit the composition onto the surface of a substrate may be a screen printing process, a flexography process, an offset printing process or a printing process using an inkjet printer or a laser printer.

The oxidizing composition intended to be printed onto the surface of the substrate may be liquid or in powder form, preferably in powder form.

According to a preferred embodiment, the oxidizing composition containing one or more oxidizing agents is printed onto the surface of the substrate by means of a laser printer or an inkjet printer.

In accordance with this preferred embodiment, the oxidizing composition is in the form of a powder.

In accordance with one embodiment, the process for preparing the substrate consists in depositing onto the surface of the substrate a composition containing the oxidizing agent(s) and then in heating the said surface to fix the powder.

In particular, the oxidizing composition is printed by means of a printing process using a laser printer onto the entire surface of the substrate, and the surface of the substrate is then selectively heated to produce one or more patterns on the said surface.

Preferably, the surface of the substrate is partially heated so as to create one or more patterns on the surface.

In accordance with another embodiment, the process for preparing the substrate consists in depositing the composition containing the oxidizing agent(s) onto the surface of a substrate, and then in removing or rendering inefficient in certain places all or part of the oxidizing agents. In this way, this process can lead towards producing one or more patterns on the surface of the substrate.

The step consisting in partially removing the oxidizing agent(s) may be performed by means of scraping, sponging, blowing, sucking or using an adhesive surface or a surface that is wetted at the places where it is desired to remove the oxidizing agent(s).

The step consisting in rendering inefficient all or part of the oxidizing agents on the surface of the substrate may be performed by means of a chemical transformation, for example a reduction, or by covering with a protective compound.

Moreover, the process for preparing the substrate may also comprise a step that consists in applying a film of starch so as to reinforce the solidity of the substrate and improve the deposition of the oxidizing agent(s) onto the surface of the substrate.

The film of starch may be thin, of the order of 2 $g/m^2$, or thick, of the order of 70 $g/m^2$.

The substrate thus pretreated in accordance with the preparation process according to the invention preferably dries within a period ranging from 5 minutes to 120 minutes, preferentially from 5 minutes to 90 minutes, more preferentially from 1 minutes to 60 minutes and better still from 5 minutes to 60 minutes.

Advantageously, in this embodiment by printing, the substrate is an element in sheet form.

The invention also relates to an element in sheet form as described previously, which is pretreated on its surface with an oxidizing composition comprising one or more oxidizing agents as described previously.

The element in sheet form may further comprise at least one layer of at least one non-absorbing material.

The element in sheet form is thus entirely or partially covered on its surface with one or more oxidizing agents.

In particular, the oxidizing agent(s) have been printed onto the element in sheet form.

The element in sheet form may be made from a nonwoven fibre material, especially a nonwoven made of cellulose or a derivative thereof. In particular, the element in sheet form may be a paper of kraft type, which has the advantage of printing well and of leading to precise patterns. Specifically, the bleached patterns obtained on the keratin fibres do not run following the application of the aqueous composition, which is preferably oxidizing.

The element in sheet form may be a sheet of plastic material which especially has the advantage of rendering well the bleaching power, which makes it possible to give bleached patterns satisfactorily. Furthermore, the sheet of plastic material does not absorb the water present in the aqueous composition, which makes it possible to avoid creating dry areas under the keratin fibres during the application of the said composition.

Hence, the plastic material in the element in sheet form corresponds to a non-absorbing material.

According to a first advantageous embodiment, the element in sheet form is a plastic sheet covered with a thin layer of paper, in particular with a thickness of less than 50 µm and more preferentially less than 30 µm, such as cigarette paper or a layer of paper that can be broken down in the presence of water, such as toilet paper, or a thin layer of hydrophilic material such as cellulose or a hydrophilic silica.

According to this embodiment, the plastic sheet corresponds to the preferably non-absorbing material layer.

In accordance with this embodiment, the layer of thin paper allows rapid drying, which prevents the lightening from running following the application of the aqueous composition, which leads to sharp bleached patterns.

In the case where a support formed from a layer of hydrophilic material is used:

the layer of hydrophilic material is typically from 5 to 200 µm thick, which allows rapid drying and prevents the bleaching from running following the application of the aqueous composition. This especially leads to sharp bleached patterns.

According to a second advantageous embodiment, the element in sheet form is a microalveolar sheet, i.e. a sheet perforated with holes that are spaced apart from each other by a plastic material. Thus, the oxidizing composition becomes housed in the holes of the substrate, which will make it possible to better render the lightening on the keratin fibres after application of the aqueous composition.

According to this embodiment, the plastic material corresponds to a non-absorbing material.

The holes are found at the surface of the element in sheet form over a thickness ranging from 10% to 90% of the thickness of the sheet.

In accordance with this embodiment, the element in sheet form also has the advantage of printing well, of better rendering the lightening leading especially to strongly bleached patterns, of not excessively absorbing the water originating from the aqueous composition and of minimizing the risks of running of the bleaching, which results in precise bleached patterns on the keratin fibres.

According to the first and second advantageous embodiments, the element in sheet form may further comprise at least one layer of at least one non-absorbing material.

Preferably, the said layer of at least one non-absorbing material is a plastic layer.

According to the first advantageous embodiment, the element in sheet form further comprises at least one layer of absorbing material.

In this embodiment, the layer of absorbing material is supported by the said layer of at least one non-absorbing material.

The following examples serve to illustrate the invention without, however, exhibiting a limiting nature.

EXAMPLE

1. Preparation of the Substrate

A sheet of aluminium foil (30 cm×10 cm) is used, on which is placed a strip of adhesive tape about 5 cm long. The foil is sprinkled with a mixture of peroxygenated salts/alkaline agent (mixture of sodium persulfate (10) and potassium persulfate (40)/sodium metasilicate (2.5)), and is then shaken to remove the non-bound powder.

The amount of powder deposited is about 5 mg/cm$^2$ at the place where the adhesive tape is on the sheet of foil.

2. Procedure

An alkaline oxidizing aqueous composition is prepared from a weight-for-weight mixture, at the time of use, of a composition sold under the name Oxydant Riche INOA 30 volumes (based on aqueous hydrogen peroxide solution) and of an alkaline composition based on 10% by weight of monoethanolamine.

A lock of a model's chestnut-brown hair is isolated using the technique of plaiting. The hair is then placed on the aluminium foil and is then pasted by applying with a brush the oxidizing aqueous composition, in an amount of 3 g, along the entire length of the lock of the hair. The edges of the foil are folded over to enclose the lock.

The composition is left to act on the lock for 50 minutes, and the lock is then removed and rinsed thoroughly. The lock of hair is washed with a shampoo and then dried.

The production of a bleached pattern is very clearly observed.

3. Preparation of the Substrate with an Inkjet Printer

A Gatocopy printer is used. One of the cartridges is filled with a freshly prepared formula containing:

10 g of sodium persulfate
40 g of potassium persulfate
5 g of sodium metasilicate
water qs 100 g A 5 cm×5 cm rectangle is printed on a sheet of office paper.

Eight prints are produced, taking care for the positioning of the sheet to allow the rectangle to be superposed on the same area.

The amount of product deposited is about 3 mg/cm$^2$.

The test as described above is then repeated.

The invention claimed is:

1. A process for lightening keratin fibers, the process comprising:
   i) applying to the keratin fibers a substrate comprising on a surface at least one first solid chemical oxidizing agent, the at least one first solid chemical oxidizing agent being deposited onto the surface of the substrate by printing, and
   ii) applying to the keratin fibers an aqueous composition comprising at least one second chemical oxidizing agent and at least one alkaline agent;
   wherein the substrate is applied first to the keratin fibers, and then the aqueous composition is applied to the keratin fibers; or
   the aqueous composition is applied first to the keratin fibers, and then the substrate is applied to the keratin fibers.

2. The process according to claim 1, wherein the substrate is an element in sheet form.

3. The process according to claim 2, wherein the element in sheet form comprises a material chosen from plastic, thermoplastic, paper, metal, aluminum, woven or nonwoven non-absorbent fibers, cellulose or derivatives thereof, or polyamide 6,6.

4. The process according to claim 2, wherein the element in sheet form comprises an adhesive layer comprising at least one first chemical oxidizing agent on a surface thereof.

5. The process according to claim 1, wherein the at least one first solid chemical oxidizing agent is chosen from urea peroxide; alkali metal bromates or ferricyanides; peroxygenated salts; or alkali metal or alkaline-earth metal persulfates, perborates, or percarbonates.

6. The process according to claim 1, wherein the at least one first solid chemical oxidizing agent is chosen from peroxygenated salts or persulfates.

7. The process according to claim 1, wherein the at least one first solid chemical oxidizing agent is present on at least a part of the surface of the substrate and represents patterns having a desired form.

8. The process according to claim 1, wherein the substrate comprises on a face opposite the surface bearing the at least one first solid chemical oxidizing agent a copy of a desired pattern.

9. The process according to claim 1, wherein the surface of the substrate comprises, prior to the deposition of the at least one first solid chemical oxidizing agent, at least one pattern.

10. The process according to claim 1, wherein the substrate is transparent.

11. The process according to claim 1, wherein the substrate further comprises on the surface at least one alkaline agent.

12. The process according to claim 1, wherein the aqueous composition comprises at least one second chemical oxidizing agent chosen from hydrogen peroxide or peroxygenated salts.

13. The process according to claim 1, further comprising preparing the substrate by depositing, via a printing method, a composition comprising at least one first solid chemical oxidizing agent onto the surface of the substrate.

14. The process according to claim 13, wherein the printing method is a screen printing process, a flexography process, an offset printing process, or a printing process using an inkjet printer or a laser printer.

* * * * *